(12) United States Patent
Yan

(10) Patent No.: US 7,931,931 B2
(45) Date of Patent: Apr. 26, 2011

(54) MEDICATED POROUS METAL PROSTHESIS AND A METHOD OF MAKING THE SAME

(75) Inventor: John Y. Yan, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 132 days.

(21) Appl. No.: 11/840,147

(22) Filed: Aug. 16, 2007

(65) Prior Publication Data

US 2007/0282427 A1 Dec. 6, 2007

Related U.S. Application Data

(60) Division of application No. 10/767,296, filed on Jan. 28, 2004, which is a division of application No. 10/235,033, filed on Sep. 3, 2002, now Pat. No. 6,723,120, which is a continuation of application No. 09/797,313, filed on Mar. 1, 2001, now abandoned, which is a division of application No. 08/837,993, filed on Apr. 15, 1997, now Pat. No. 6,240,616.

(51) Int. Cl.
*A61L 33/00* (2006.01)
*B05D 3/02* (2006.01)
*B05D 1/12* (2006.01)
*B05D 1/36* (2006.01)
*A61F 2/06* (2006.01)

(52) U.S. Cl. ....... 427/2.1; 427/2.24; 427/2.25; 427/180; 427/201; 427/202; 427/205; 623/1.11; 623/1.39; 623/1.4; 623/1.42; 623/1.43; 623/1.44

(58) Field of Classification Search .............. 427/2.1, 427/2.24, 2.25, 2.28, 180, 201, 202, 205; 623/1.1, 1.39, 1.42, 1.43, 1.44

See application file for complete search history.

(56) References Cited

U.S. PATENT DOCUMENTS

| | | | |
|---|---|---|---|
| 4,073,999 A * | 2/1978 | Bryan et al. | 428/312.8 |
| 4,101,984 A | 7/1978 | MacGregor | |
| 4,321,711 A | 3/1982 | Mano | |
| 4,355,426 A | 10/1982 | MacGregor | |
| 4,374,669 A * | 2/1983 | Mac Gregor | 419/9 |
| 4,405,319 A | 9/1983 | Cosentino | |
| 4,458,366 A * | 7/1984 | MacGregor | 623/3.13 |
| 4,693,721 A | 9/1987 | Ducheyne | |
| 4,729,871 A | 3/1988 | Morimoto | |
| 4,760,849 A | 8/1988 | Kropf | |
| 5,015,253 A | 5/1991 | MacGregor | |
| 5,163,958 A * | 11/1992 | Pinchuk | 623/23.49 |
| 5,171,262 A | 12/1992 | MacGregor | |
| 5,342,348 A * | 8/1994 | Kaplan | 604/891.1 |
| 5,370,682 A | 12/1994 | Schmitt | |
| 5,419,760 A | 5/1995 | Narciso | |
| 5,433,909 A | 7/1995 | Marakos et al. | |
| 5,437,834 A | 8/1995 | Okimatsu et al. | |
| 5,441,515 A | 8/1995 | Khosravi et al. | |
| 5,477,864 A * | 12/1995 | Davidson | 600/585 |
| 5,492,768 A | 2/1996 | Okimatsu et al. | |
| 5,540,712 A | 7/1996 | Kleshinski et al. | |
| 5,607,463 A * | 3/1997 | Schwartz et al. | 623/1.44 |

(Continued)

*Primary Examiner* — Timothy H Meeks
*Assistant Examiner* — Cachet I Sellman
(74) *Attorney, Agent, or Firm* — Squire, Sanders & Dempsey (US) LLP

(57) ABSTRACT

A porous prosthesis for delivering a medication to the site of implantation, and a method of making the same, is disclosed.

30 Claims, 5 Drawing Sheets

U.S. PATENT DOCUMENTS

| | | | |
|---|---|---|---|
| 5,641,443 A * | 6/1997 | Calcote et al. | 264/127 |
| 5,697,967 A | 12/1997 | Dinh et al. | |
| 5,707,385 A | 1/1998 | Williams | |
| 5,755,771 A | 5/1998 | Penn et al. | |
| 5,769,884 A * | 6/1998 | Solovay | 623/1.13 |
| 5,800,512 A | 9/1998 | Lentz et al. | |
| 5,879,398 A | 3/1999 | Swarts et al. | |
| 5,928,279 A | 7/1999 | Shannon et al. | |
| 5,945,029 A | 8/1999 | Scholz et al. | |
| 5,972,027 A * | 10/1999 | Johnson | 623/1.42 |
| 6,010,529 A | 1/2000 | Herweck et al. | |
| 6,027,779 A | 2/2000 | Campbell et al. | |
| 6,165,210 A | 12/2000 | Lau et al. | |
| 6,287,337 B1 | 9/2001 | Martakos et al. | |

\* cited by examiner

MEDICATED POROUS METAL PROSTHESIS AND A METHOD OF MAKING THE SAME

CROSS REFERENCE

This is a divisional application of application Ser. No. 10/767,296, filed on Jan. 28, 2004, which is a divisional of application Ser. No. 10/235,033, filed on Sep. 3, 2002 now U.S. Pat. No. 6,723,120, which is a continuation of application Ser. No. 09/797,313, filed on Mar. 1, 2001, now abandoned, which is a divisional of application Ser. No. 08/837,993, filed on Apr. 15, 1997, now U.S. Pat. No. 6,240,616.

FIELD OF THE INVENTION

This invention generally relates to a medicated prosthesis or implant, and a method of making the same. More particularly, the invention relates to a porous prosthesis, such as a stent, that can be planted in the vasculature of a patient and can deliver a therapeutic agent to the site of implantation.

DESCRIPTION OF RELATED ART

Stents are generally cylindrically shaped prosthetic implants which function to hold open and sometimes expand a segment of a blood vessel or other anatomical lumen. They are particularly suitable for supporting and preventing a torn or injured arterial lining from occluding a fluid passageway. Intravascular stents are very useful for treatment of coronary artery stenoses, and for reducing the likelihood of the development of restenosis or closure after balloon angioplasty.

The success of a stent can be assessed by evaluating a number of factors, such as the degree of development of thrombosis; degree of neointimal hyperplasia or smooth muscle cell migration and proliferation following implantation of the stent; severity of injury to the artery wall; overall loss of luminal patency; stent diameter in vivo; thickness of the stent; and leukocyte adhesion to the luminal lining of stented arteries. However, the chief areas of concern are early subacute thrombosis, and eventual restenosis of the blood vessel due to intimal hyperplasia.

Therapeutic pharmacological agents have been developed to improve successful placement of the stent and are delivered to the site of stent implantation. Stents that are of a common metallic structure were previously unable to deliver localized therapeutic pharmacological agents to a blood vessel at the location being treated with the stent. There are polymeric materials that can be loaded with and release therapeutic agents. However, these polymeric materials may not fulfill the structural and mechanical requirements of a stent, especially when the polymeric materials are loaded with a drug, since drug loading of a polymeric material can significantly reduce the structural and mechanical properties of the polymeric material.

It has been known in the art to coat a metallic stent with a polymeric material and load the polymeric material with a drug. Alternatively, stents of polymeric materials have been reinforced with metal structure. These stent designs have the strength necessary to hold open the lumen of the vessel because of the reinforced strength of the metal. Stents made of both polymeric material and metal have a larger radial profile because the volume occupied by the metal portion of the stent cannot absorb and retain drugs. Reducing the profile of a stent is preferable because it increases the in vivo diameter of the lumen created by the stent. Thus it is desirable to configure a metallic stent to deliver drugs to the blood vessel walls without substantially increasing the profile of the stent. The present invention meets these needs.

SUMMARY

In an aspect of the present invention, a method of manufacturing a stent is provided, including attaching a first group of particles together to form a first porous network; and attaching a second group of particles together and to the first porous network to form a second porous network, wherein the average particle size of the first group is greater than the average particle size of the second group so that the first porous network has an average pore size that is greater than the average pore size of the second porous network. In one embodiment, the method additionally includes depositing a therapeutic substance in the first porous network, wherein the second porous network reduces the rate of release of the substance from the stent after the stent has been implanted in a body of a patient. In another embodiment, the method further includes depositing a polymeric film layer on the second porous network. In a further embodiment, the particles of the second group are attached all the way around the first porous network such that the second porous network completely surrounds the first porous network.

In another aspect of the invention, a method of manufacturing a stent is provided, including sintering elongated fibers together to form a component of a stent body.

In a further aspect, a method of manufacturing a stent is provided including forming a first porous region; forming a second porous region disposed over a portion of the first porous region; and depositing a therapeutic substance in the first porous region, wherein an average pore size of the second porous region is less than an average pore size of the first porous region. In one embodiment, the second porous region is for contacting the wall of a vessel when the stent has been implanted in the vessel. In another embodiment, the method further includes forming a third porous region over a portion of the first porous region such that the first porous region is between the second and third porous regions. In a further embodiment, the first or second porous region is formed by sintering particles. In yet another embodiment, the first porous region is formed by sintering particles having a first average diameter, and the second porous region is formed by sintering particles having a second average diameter, wherein the first average diameter is larger than the second average diameter.

In another aspect, a method of manufacturing a stent is provided, including forming a first porous region; forming a second porous region disposed over a first portion of the first porous region; forming a third porous region disposed over a second portion of the first porous region; and depositing a therapeutic substance in the first porous region; and wherein an average pore size of the second porous region and an average pore size of the third porous region is less than an average pore size of the first porous region for reducing a rate of release of the therapeutic substance from the first porous region after the stent has been implanted in a vessel.

In yet a further aspect, a method of manufacturing a strut element for a stent is provided, including placing metallic particles having an average first diameter in contact with each other; sintering the metallic particles having the average first diameter to form an inner core; placing metallic particles having an average second diameter on the inner core; and sintering the metallic particles having the average second diameter to form a porous outer layer. In one embodiment, the average second diameter is less than the average first diameter. In another embodiment, the method further includes depositing a therapeutic substance in the inner core.

In another aspect, a stent is provided including a strut element wherein the strut element includes a solid metallic inner core and an outer layer disposed over the inner core, the outer layer being made from a porous metallic material. In one embodiment, the porous metallic material is made from sintered particles, filaments or fibers. In another embodiment, the outer layer is capable of holding a therapeutic substance for releasing of the substance after the stent has been implanted in a vessel.

In yet a further embodiment, a stent is provided including a solid metallic region and a porous metallic region disposed on the solid metallic region. In one embodiment, the porous metallic region is made from sintered particles, filaments or fibers.

In another embodiment, a method of manufacturing a strut element for a stent is provided, including applying metallic particles onto a solid inner core; and sintering the metallic particles to form a porous outer layer disposed over a portion of the solid inner core.

In a further aspect of the present invention, a method of manufacturing a sintered sheet element for a stent is provided, including placing metallic particles having an average first diameter to a first surface of a metallic core layer; placing metallic particles having an average second diameter to a second surface of the metallic core layer; sintering the metallic particles having the average first diameter to form a first porous outer layer; and sintering the metallic particles having the average second diameter to form a second porous outer layer. In one embodiment, the first and second porous outer layers are on opposing sides of the metallic core layer. In another embodiment, the metallic core layer is a porous substrate. In yet another embodiment, the metallic core layer is a solid substrate. In a further embodiment, the method additionally includes applying a therapeutic agent to the first porous outer layer or the second porous outer layer after the formation of the first and second porous outer layers.

DETAILED DESCRIPTION

Figure 1:
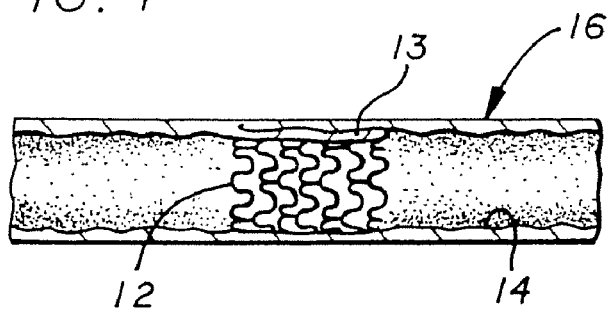
FIG. 1 is a longitudinal sectional view of a blood vessel with a stent manufactured according to one embodiment of the present invention.
Figure 2:
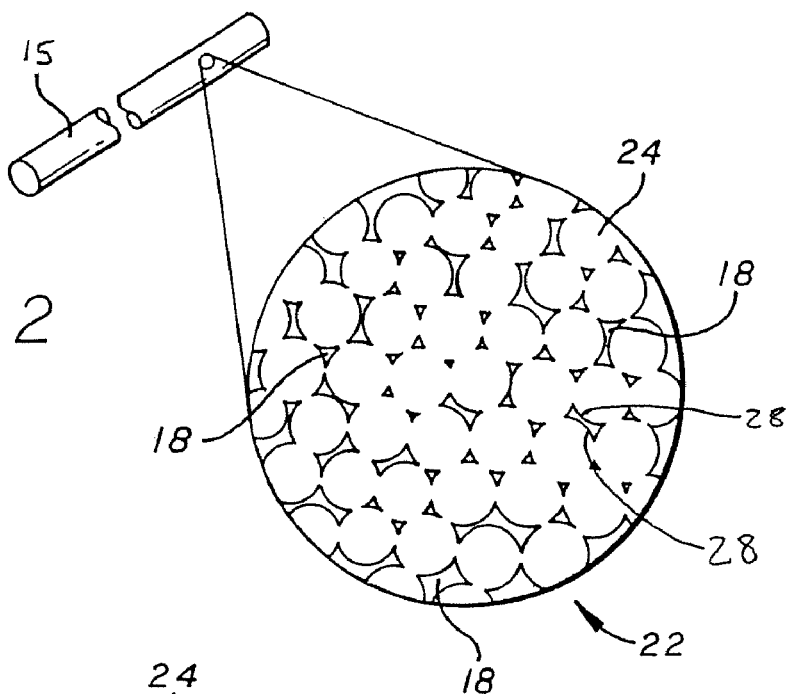
FIG. 2 is a magnified, partially cut away perspective view of a porous stent wire or strut manufactured according to one embodiment of the present invention.

Referring now to FIG. 1, the prosthesis of one embodiment is a porous stent 12 that is radially expandable against a wall 14 of a vessel 16. The stent 12 is loaded with a therapeutic agent in porous cavities or pores 18 (FIG. 2) of the stent 12. When placed in the vasculature, the therapeutic agent is delivered to the tissue that comes into contact with the stent 12. The stent 12 of one preferred embodiment is formed of a stent wire 15 that is porous. An example of the wire 15 is a sintered metal wire. FIG. 2 illustrates a partial microscopic view of the sintered wire 15 that is suitable for use in one embodiment of the present invention. The wire 15 has porous cavities 18. The size of the cavities or pores 18 preferably ranges between 0.01 and 20 microns.

Porous metal is made, according to one preferred embodiment, by the process of sintering metal. Sintering is a process where particles 24 are bonded together without entirely melting the particles 24. The particles 24 are pressed together or molded into a desired shape. A considerable amount of pressure is first applied to press the particles 24 together. The metal is then heated to temperatures slightly below the melting point of the metal. Without entirely melting, the particles 24 bond to each other at their respective surfaces. Space remains between a lattice 22 of the particles 24 which define the cavities or pores 18.

Figure 3:
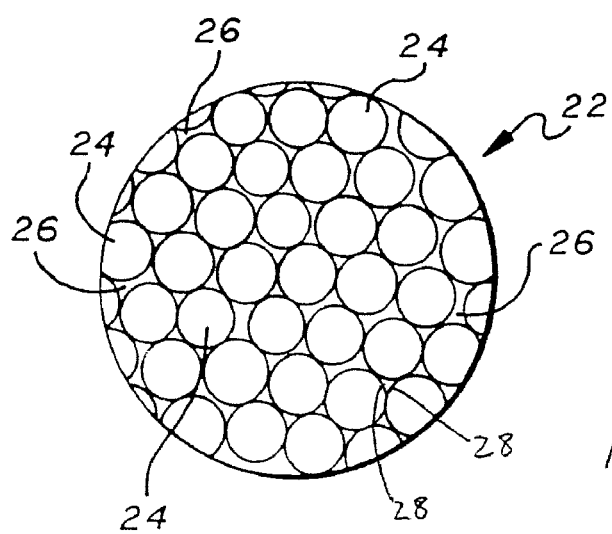
FIG. 3 is a magnified, cross-sectional view of unsintered packed particles.

The formation of sintered metal is illustrated with reference to FIG. 3 and continued reference to FIG. 2. FIG. 3 is a microscopic view of a packed lattice 22 of the metallic particles 24. Gaps 26 exist between each particle 24 despite the fact that the particles 24 are pressurized and are in contact with adjacent particles 24. The particles 24 are preferably sized between 0.02 microns (6 nm) and 20 microns (0.5 μm) in diameter. Prior to heating, there are no chemical bonds formed between the individual particles 24. When the metal is heated to slightly below the melting point of the metal, the particles 24 bond with neighboring particles 24. The gaps 26 in the packed lattice 22 form pores 18 when the particles 24 are sintered. Thus in FIG. 2, the metal stent wire 15 formed by the process of sintering has the porous cavities 18 extending throughout the entire wire 15, thereby interconnecting the cavities 18. The cavities 18 then can be filled with a therapeutic agent as hereinafter described. The appropriate pressure and temperature of sintering a particular metal is specific to that particular metal. One skilled in the art of metal fabrication understands how to sinter any given metal or alloy.

For each of the embodiments, the metal stent material can be any suitable metal such as stainless steel, tantalum, nickel-titanium alloy, platinum-iridium alloy, molybdenum-rhenium alloy, gold, magnesium, or combinations thereof, although other similar materials also may be suitable. The metal can be modified to exhibit different hardnesses, and thus varying stiffnesses, by well known annealing and manufacturing processes.

One of the most important factors to be considered when making a stent according to one embodiment of the present invention is the porosity of the metal. Porosity is the total volume of pores in the sintered metal divided by the total volume of the metal. Porosity determines the amount of a therapeutic agent that can be loaded into the stent 12 of predetermined dimensions. High porosity means that the stent 12 can deliver more therapeutic agents or have a narrower profile because the stent 12 is less dense. High porosity, according to some embodiments of the present invention, adversely affects the strength and elasticity of a metal. Consequently, there is an ongoing tradeoff between stent strength, on the one hand, and stent profile and stent load capacity on the other hand.

Pore size is a function of particle size and dimension. In one embodiment of the present invention illustrated in FIG. 3, the particles 24 are generally spherical. Size of the pores 18, particularly with generally spherical particles 24, is proportional to particle size. When the particles 24 have inconsistent size, smaller particles tend to fill the gaps 26 between the larger particles 24. Thus, the porosity of such particles 24 is less predictable. Consistent pore size is also important to ensure that drugs are evenly distributed throughout the stent 12. Consistent distribution on the other hand ensures that the tissue in contact with the stent 12 will receive an even distribution of the therapeutic agent.

There are several types of drugs that can be administered by the stent 12 when placed in the vessel. Examples of therapeutic drugs, or agents include antiplatelets, antifibrins, antithrombins and antiproliferatives. Examples of anticoagulants, antiplatelets, antifibrins, and antithrombins include but are not limited to sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen, Inc., Cambridge, Mass.), and 7E-3B® (an antiplatelet drug from Centocore, Inc., Mavern, Pa.). Examples of cytostatic or antiproliferative agents include angiopeptin (a somatostatin analogue from Beaufour Ipsen S.A., Paris, France), angiotensin converting enzyme inhibitors such as Captopril® (available from Bristol-Myers Squibb Co., New York, N.Y.), Cilazapril® (available from Hoffmann-La Roche Inc., Nutley, N.J.), or Lisinopril® (available from Merck & Co., Inc., Whitehouse Station, N.J.), calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck & Co., Inc.), methotrexate, monoclonal antibodies (such as to PDGF receptors), nitroprusside, phosphodiesterase inhibitors, prostaglandin inhibitor (available from GlaxoSmithKline plc, Middlesex, United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon and genetically engineered epithelial cells, for example.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agent are known in the art. Furthermore, the calculation of dosages, dosage rates and appropriate duration of treatment are previously known in the art.

The therapeutic agent of one embodiment is preferably in liquid form and is loaded into the stent 12 by immersing the stent 12 in a medicated solution. The therapeutic agent may be dissolved in a solvent or suspended in a liquid mixture. If a suspension of drugs is used, it is important that the pore size of the stent 12 is considerably larger than the therapeutic agent. An average pore size that is more than ten (10) times the particle size of a suspended therapeutic agent is suitable. After the stent 12 is immersed in the medicated solution, the therapeutic agent absorbs into the pores of the stent 12. At which time, the loaded stent 12 can be removed from the solution and implanted into the vasculature of a patient. Additionally, a therapeutic agent can be loaded into the stent 12 by applying pressure to the fluid to aid the passage of the medicated fluid into the pores 18 of the stent 12. This can be done similar to how fluid can be pressurized through the pores of a filter.

Once loaded, the therapeutic agent remains in place by the surface tension between walls 28 of the several porous cavities 18 and the therapeutic agent. As shown in FIG. 1, the loaded or medicated stent 12 is then deployed to the site of arterial closure 13 and is expanded. The expanded stent 12 engages the walls 14 of the vessel 16 to maintain the patency of the vessel 16. Once in the vessel 16, the therapeutic agent disseminates from the porous cavities 18 of the stent 12 and is absorbed into the tissue of the walls 14 of the vessel 16 that are in contact with the stent 12.

The advantage of the stent 12 of the present invention over prior art medicated stents is one of profile and strength. Metal, including sintered metal, is stronger than synthetic materials that are capable of being loaded with a therapeutic agent. Thus, in order for a medicated stent to deliver an appropriate amount of a therapeutic agent and structurally maintain vessel patency, the profile of the stent must be substantially larger than metal stents. This is true whether a metal stent is coated with a therapeutic agent, or if the stent is entirely made of a plastic material.

Sintered metal has strength and elasticity that is comparable to regular metal. Sintered metal furthermore has the added feature that it is porous. Consequently, a sintered stent can be made having a profile that is substantially comparable to a conventional metal stent. Yet, a therapeutic agent can be loaded into the pores and delivered to the site of stent implantation without the aid of medicated coatings.

Additionally, many synthetic materials, including materials that are bioabsorbable, cause inflammation of the tissue. A medicated stent that has a therapeutic agent loaded directly into the pores 18 of the stent 12 can avoid synthetic coatings that have been known to cause irritation at the site of stent implantation.

Figure 4:
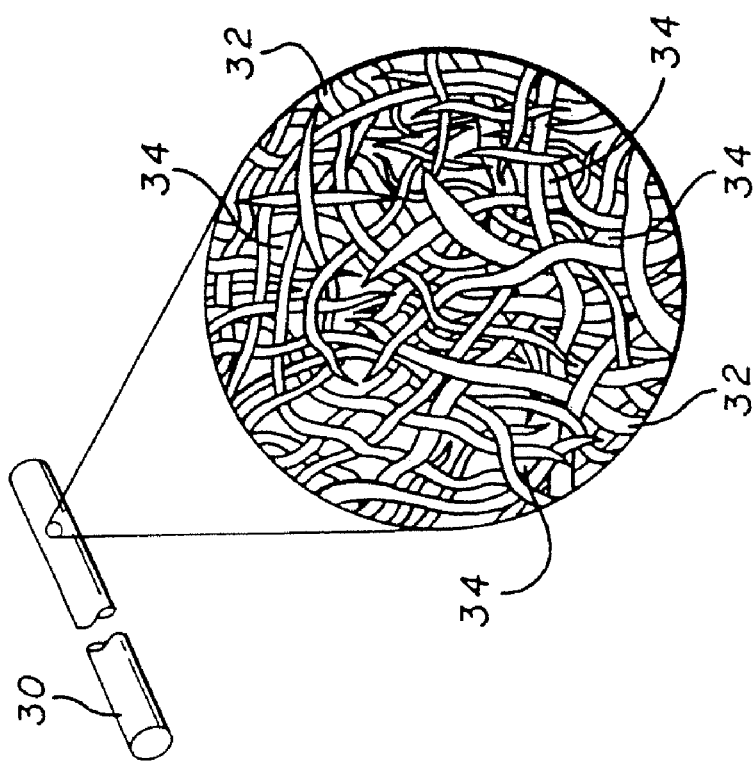
FIG. 4 is a porous stent wire or strut in partially magnified, partially cut away perspective manufactured according to one embodiment of the present invention.

FIG. 4 illustrates an alternative embodiment of a stent wire 30 constructed according to the present invention. The stent 12 is formed of elongated particles, i.e., filaments or fibers 32. Sintered particles 24 that are generally spherical in shape are capable of forming sintered metal having a porosity in the range of 0.30 to 0.05. However, when filaments or fibers 32 are sintered, the porosity can be increased above 0.30. The technique of fabricating a stent with elongated filaments or fibers 32 is similar to the method described above for spherical particles 24 or powders. The filaments or fibers 32 are molded and pressurized. Then the filaments or fibers 32 are heated to a temperature just below the melting point of the metal.

Greater porosity of the stent 12 made of metal filaments or fibers 32, rather than spherical particles 24, is obtained because of the irregular shape of the filaments or fibers 32. The filaments or fibers 32 cannot be packed as tightly as regular generally spherical particles 24. Furthermore, the filaments or fibers 32 can be packed less densely and still maintain contact between the filaments or fibers 32 to allow sintering. Thus, the void space or pores 34 in the sintered metal are larger.

The strength of the stent wire 30 using filaments or fibers 32 in FIG. 4 is improved because the individual strands have larger surface area to volume and contact a greater number of neighboring strands. Thus, each filament or fiber 32 will have a larger bonding surface and may bond with a greater number of neighboring filaments or fibers 32. A matrix of overlapping filaments or fibers 32 is thus formed with greater porosity and stronger inter-particle bonding.

Figure 5:
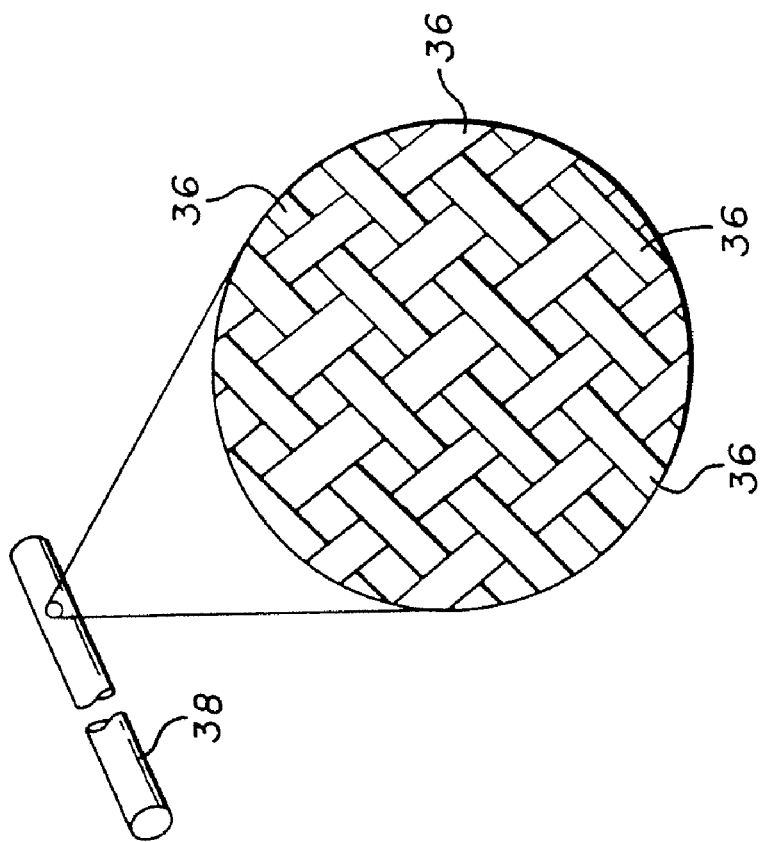
FIG. 5 is a porous stent wire or strut in partially magnified, partially cut away perspective manufactured according to one embodiment of the present invention.

In yet another embodiment, wire fibers 36 are woven or twined into a structure 38 as illustrated in FIG. 5. The individual strands cooperate in a synergistic manner to reinforce the strength of the wire 38. Additionally, the wire fibers 36 can be woven into the form of a sintered metal sheet having improved and reinforced strength or a sintered metal tube. Other combinations of particle size and shape can be employed to form a stent wire having different characteristics.

Figure 6:
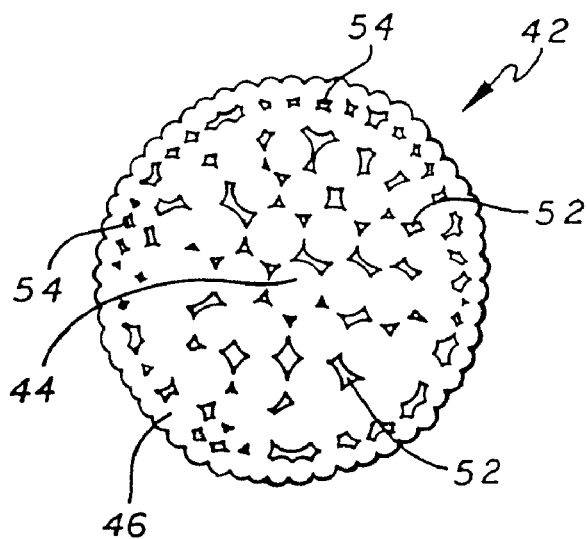
FIG. 6 is a cross-sectional view of a stent wire or strut manufactured according to one embodiment of the present invention.

In another embodiment illustrated in FIG. 6, a stent wire 42 is formed of an inner core 44 and an outer layer or core 46 of the particles 24. The outer layer 46 is formed from the particles 24 having a different diameter than the diameter of the particles 24 that form the inner core 44. For example, the core 44 of the metal is formed of particles that have a diameter in the range of 10-20 microns at the core of the wire 42. Surrounding the core 44 are particles that have a diameter in the range of 2-4 microns on the outer layer 46. The larger particles create the core 44 having larger pores 52. This results in higher porosity and thus a higher load capacity. The smaller particles on the outer layer 46 form smaller pores 54 which reduce the rate of diffusion of drugs into the tissues of a vessel.

When a therapeutic agent is loaded into the stent 12 formed of the wire 42 illustrated in FIG. 6, a larger volume can be stored in the larger pores 52 at the core 44 of the wire 42. Once the stent 12 is placed into a vessel, the therapeutic agent in the stent wire 42 is delivered at a rate determined by the smaller pores 54 in the outer layer 46 of the stent wire 42. Such a structure is expected to have a benefit of being able to store a large amount of a therapeutic agent at the core 44 and deliver the therapeutic agent at a slower rate. Consequently, this design is desirable for low-dose, long-term drug therapy.

Figure 7:
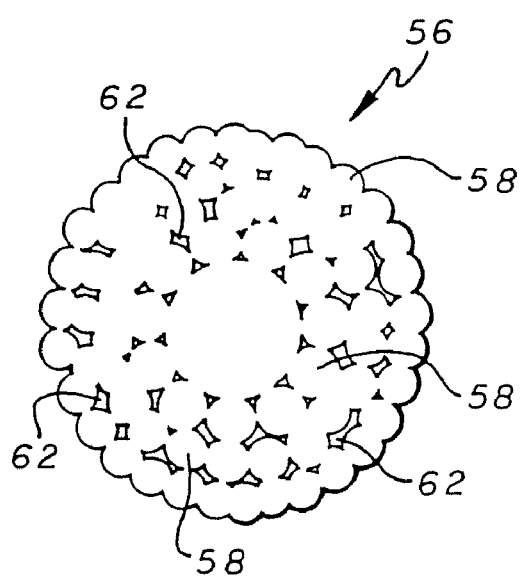
FIG. 7 is a cross-sectional view of a stent wire or strut manufactured according to one embodiment of the present invention.

Alternatively, according to another embodiment of the present invention shown in FIG. 7, a stent wire 56 is formed from sintered metal particles 58. The pores 62 formed between the sintered particles 58 surrounding a solid core retain the therapeutic agent. The total porosity of the stent wire 56 having the solid core and porous outer layer is much lower than a stent wire of similar proportion that is entirely made of sintered particles. However, the solid core reinforces the tensile strength and elasticity of the metal stent and is considerably stronger. Thus, it is desirable to use a sintered stent with a solid core for applications where maximum tensile strength and elasticity is desirable and only a relatively small amount of therapeutic agent is needed.

Figure 8:
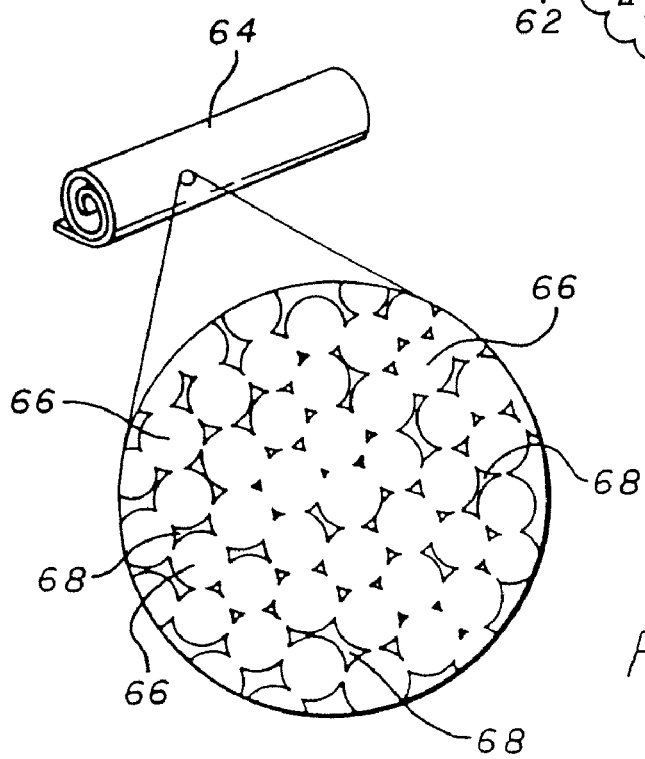
FIG. 8 is a partially magnified perspective of a stent formed from a sheet of sintered metal according to one embodiment of the present invention.

The sintered metal stent of yet another embodiment of the present invention can be made of material formed in different shapes than sintered metal. For example, the stent can be formed of a sheet of sintered metal as shown in FIG. 8 or a sintered metal tube 64. By way of example, metal particles 66 are arranged and pressurized into the sheet 64. The sheet 64 is heated to a temperature below the melting point of the particles 66 as described previously. The sheet 64 of sintered metal is porous as illustrated by reference number 68.

The same principles that apply to porosity and pore size of a wire apply equally to a sintered stent that is formed into a sheet or tube. The advantage of forming the stent from a sheet of metal is that the stent is radially expandable without placing a great deal of strain on the metal lattice when it is expanded. A sheet or tube of sintered metal can be cut in the desired shape to form the metal structural member with a laser, such as a continuous $CO_2$ laser, a pulsed YAG laser, or an excimer laser, for example, or alternatively, by chemical etching or stamping. When cut from a flat sheet, the stent is then rolled into a cylindrical configuration and laser welded along the longitudinal edges.

Figure 9:
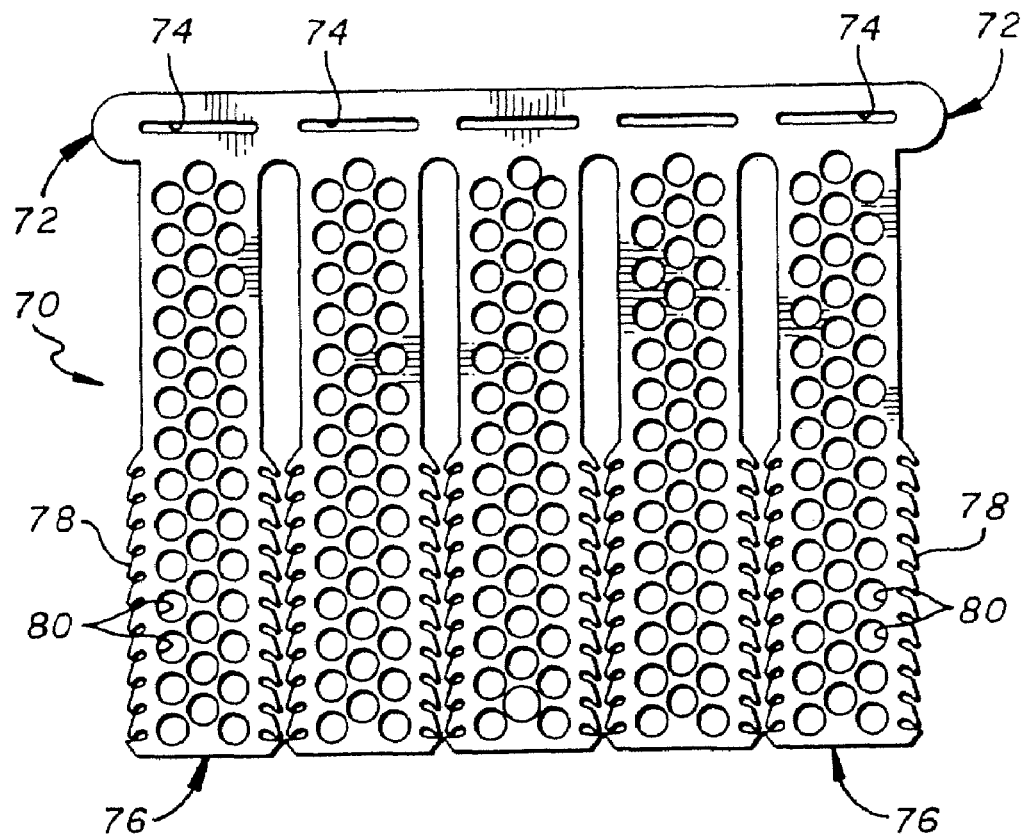
FIG. 9 is a sheet of sintered metal manufactured according to one embodiment of the present invention.

The stent can be formed into any particular pattern. One such pattern is a rolled locking design and is illustrated in FIG. 9. A sheet 70 is etched into a configuration that has a head portion 72 that includes one or more slots 74 for receipt of a like number of tail portions 76. The tail portions 76 are received into the slots 74 so as to form a cylindrical loop. The tail portions 76 include a plurality of teeth 78 adapted to cooperatively engage the slots 74 of the head portion 72. When the teeth 78 engage the slots 74, the tail portions 76 are retained in place in an expanded state. Additionally, holes 80 are formed throughout the stent to reduce the metal to air ratio of the stent. The less metal in contact with the wall of the vessel, the better the blood compatibility of the stent.

Prior to deployment, the tail portions 76 are coiled into a retracted position. The tail portions 76 are threaded through the slots 74 and wound. The stent is expanded by a balloon according to principles that are well known in the art for delivering and implanting a stent. As the stent is expanded by a balloon during deployment, the stent unwinds and the teeth 78 lock into the slots 74 at a desired radial diameter to prevent the stent from returning to its original retracted state.

A benefit of the coiled stent shown in FIG. 9 is that the stent can be etched to have a minimal surface area that comes in contact with the walls of the vessel. This may be an important feature when it is desired to cover an entire portion of the walls of a blood vessel with a therapeutic agent because the coiled sheet metal stent can be configured to maintain maximum surface area contact with the wall of the blood vessel in contrast to wire stents.

Figure 10:
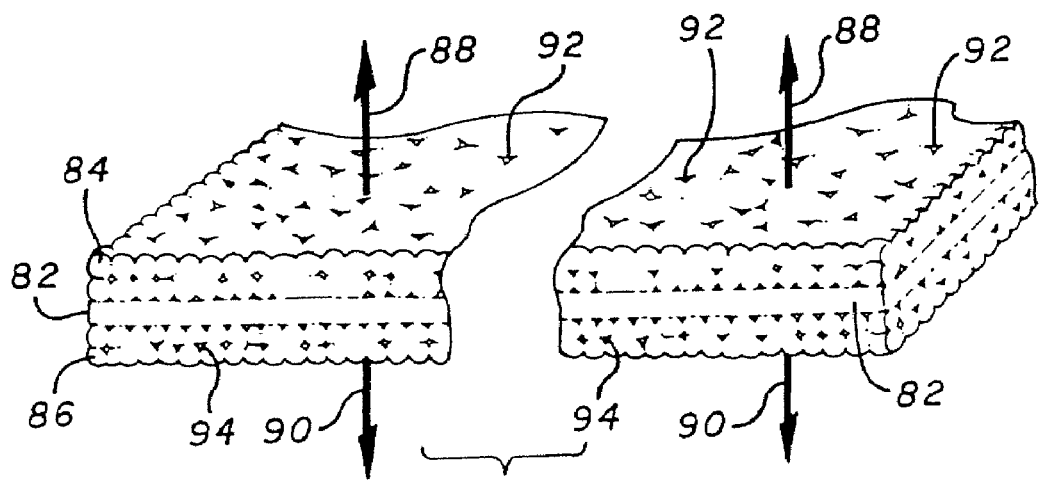
FIG. 10 is a cross-sectional, partially cut away view of a sheet of sintered metal manufactured according to the principles of one embodiment of the present invention.

With reference to FIG. 10, another embodiment of the present invention is a sheet formed of sintered particles that are sintered to top and bottom sides 84 and 86 of a metal sheet 82. The sheet 82 of FIG. 10 is similar in structure to the stent wire 56 of FIG. 7 that has the solid core and has porous particles sintered to the core forming a porous outer layer. The solid core reinforces the strength of the metal. The metal sheet 82 also provides a barrier through which a therapeutic agent cannot pass. Thus, a therapeutic agent loaded into the pores 92 on the top side 84 of the sheet 82 permeates in a first direction 88 outward from the solid core. A therapeutic agent loaded into the pores 94 on the bottom side 86 of the solid core permeates only in a second direction 90 opposite to the direction of the therapeutic agent loaded into the pores 92 on the top side 84.

When a stent made of the sheet of FIG. 10 is looped into a cylindrical formation and placed into a vessel, only the top side 84, which is directed radially outward, engages the wall of the vessel. The bottom side 94 faces radially inward and does not come in contact with the wall of the vessel. Thus, if it is desired, a first therapeutic agent can be loaded into the top side 84 to treat the tissues of the wall of the vessel. A second therapeutic agent can be loaded into the bottom side 86 to prevent coagulation of the blood flowing in the vessel. Additionally, the stent can be formed so that the particles are sintered only to one side 84 or 86 of the stent. A therapeutic agent is loaded into the sintered metal on the porous side 84 or 86 of the stent. When a stent is formed from a one-sided porous sheet, the porous side can be oriented radially outward to deliver a therapeutic agent to the tissues of the wall of the vessel.

Figure 11:
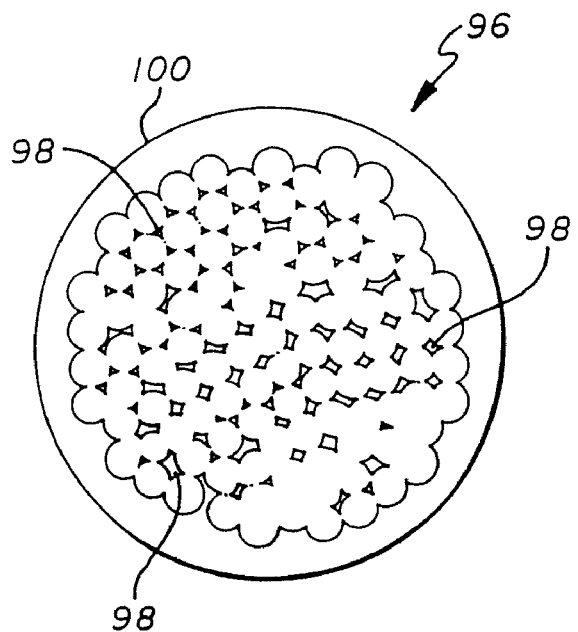
FIG. 11 is a cross-sectional view of a stent wire or strut manufactured according to the principles of one embodiment of the present invention.

FIG. 11 illustrates a cross-sectional view of a stent wire 96 according to another embodiment of the invention. The stent wire 96 has a plurality of porous cavities or pores 98. A therapeutic agent is loaded into the pores 98 of the sintered metal. Then, a coating 100 is applied to the sintered metal. The coating 100 may be used for several purposes as illustrated hereinafter.

Figure 12:
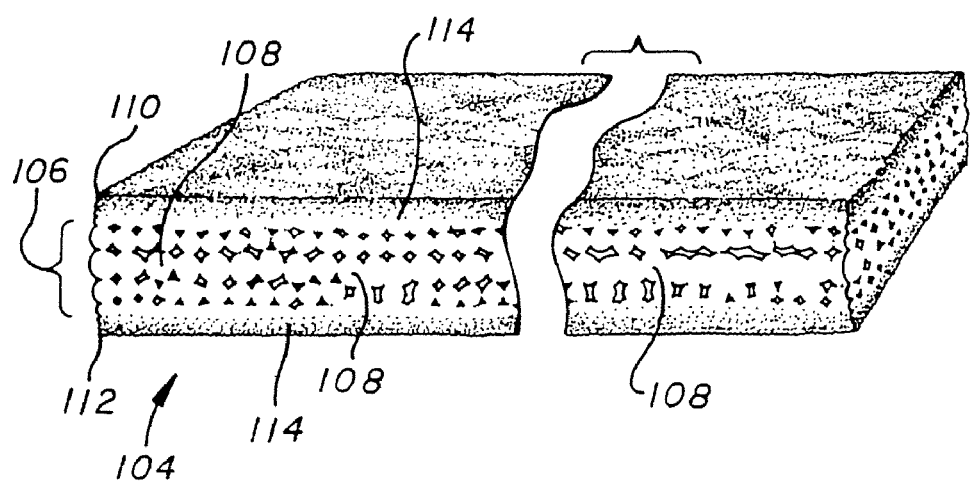
FIG. 12 is a cross-sectional view, partially cut away of a sheet of sintered metal manufactured according to the principles of one embodiment of the present invention.

With reference to FIG. 12, another embodiment of the invention is shown wherein the stent is formed of a sintered sheet 104 of metal having a middle core layer 106 formed of large diameter particles 108 that form large pores. The core layer 106 is sandwiched between top and bottom layers 110 and 112 formed of smaller diameter particles 114 or particles that form smaller diameter pores. The sheet 104 is formed by orienting the core layer 106 of the large diameter particles 108 along a plane. The top layer 110 of smaller diameter particles 114 is arranged in a plane parallel to and above the core middle layer 106. The bottom layer 112 of the particles 114 is arranged in a plane parallel to and below the core middle layer 106. The three layers 106, 110, and 112 are pressed together and sintered into the single sheet 104. The sheet 104 can then be cut or etched into a stent configuration.

While one of the benefits of the present invention is to provide a stent that does not require a coating for the purpose of delivering a therapeutic agent, the application of a coating after a therapeutic agent is loaded into the pores of the sintered metal does not defeat the utility of the present invention. For example, when a therapeutic agent is loaded into the pores of the stent and into a polymeric coating, the profile of the polymeric coating can be reduced. Alternatively, a larger dosage of a therapeutic agent can be delivered to the site of stent implantation. Additional benefits are observed by loading a stent with a therapeutic agent in the pores of the metal and then further applying a coating to the stent. Furthermore, even if a coating is applied to the stent, the principles of reducing profile and reinforcing the stent are still apparent because a greater volume of a therapeutic agent can be delivered by a coated sintered stent than a coated, solid stent having comparable dimensions.

The polymeric material that coats a sintered metal stent of the invention preferably comprises a biodegradable, bioabsorbable polymeric film that is capable of being loaded with and capable of releasing therapeutic drugs. The, polymeric coatings preferably include, but are not limited to, polycaprolactone (PCL), poly(DL-lactic acid) (DL-PLA) and poly(L-lactic acid) (L-PLA) or lactide. Other biodegradable, bioabsorbable polymers such as polyorthoesters, polyiminocarbonates, aliphatic polycarbonates, and polyphosphazenes may also be suitable, and other non-degradable polymers capable of carrying and delivering therapeutic drugs may also be suitable. Examples of non-degradable synthetic polymers are polyurethane, polyethylene, polyethylene teraphthalate, ethylene vinyl acetate, silicone and polyethylene oxide (PEO). The polymeric layers, according to one embodiment, are to be loaded with a pharmacologic agent for use in localized drug therapy. As used in this description, the terms biodegradable, bioabsorbable, reabsorbable, degradable, and absorbable are meant to encompass materials that are broken down and gradually absorbed or eliminated by the body, whether these processes are due to hydrolysis, metabolic processes, or bulk or surface erosion. In each of the foregoing embodiments, one polymeric layer is preferably about 0.0001 to 0.002 inches thick.

The thin polymeric films used to coat the stent are preferably first intermixed with the drug or drugs to be delivered, and then are typically laminated or solvent cast to the surface of the metal structural member. Lamination processing methods and temperatures can vary widely depending on the polymers used and the temperature sensitivity of the loaded drugs. Alternatively, the metal structure of the stent can be encapsulated in the layers of polymeric material by solvent casting, melt processing, insert molding, and dip coating.

In one embodiment of the present invention, the coating 100 is bioabsorbable, but no therapeutic agent is loaded into the polymer. The coating 100 dissolves after implantation and this delays the time that the therapeutic agent is released into the vasculature of a patient. The thickness of the coating 100 as well as the rate at which the coating 100 is bioabsorbed determines the length of time that the stent is mounted into the vasculature before the therapeutic agent is delivered from the pores of the stent. Additionally, a therapeutic agent can be loaded into the bioabsorbable coating 100. Thus a therapeutic agent will be delivered by the stent at a rate determined by the bioabsorbability of the coating 100. Once the bioabsorbable material has completely dissolved, the therapeutic agent in the pores can be delivered at a rate determined by the pore size and porosity.

In another embodiment, it is preferred that the coating 100 is permeable and non-absorbable. In such circumstances, the rate at which the drugs permeate into the tissue is controlled by the physical properties of the particular coating 100 selected. Additionally, the coating 100 may be selected to reduce restenosis, thrombosis or other tissue inflammation. For example, a heparin coating is known in the art to reduce blood clotting. Heparin, when coated on a stent reduces clotting of blood on the surface of the stent. The heparin coating is affixed to the surface of the stent through ionic bonding, end point attaching, or photo-linking the heparin.

In yet another embodiment, a first therapeutic agent is loaded into the coating 100 and a second therapeutic agent is loaded into the pores of the stent. This may be the case when a series of drug dosages or concentrations are needed. When such a stent is placed into the vasculature, the first therapeutic agent is absorbed first by the vasculature and the second therapeutic agent is absorbed later by the vasculature. This variation adds a further dimension to drug treatment allowing for sequential drug therapy at the site of placement of the stent.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of manufacturing a stent, comprising:
   attaching a first group of particles together to form a first porous network; attaching a second group of particles together and to the first porous network to form a second porous network; and
   attaching a third group of particles together and to the first porous network to form a third porous network, wherein the first porous network is positioned between the second and third porous networks,
   wherein the average particle size of the first group is greater than the average particle size of the second group so that the first porous network has an average pore size that is greater than the average pore size of the second porous network, and wherein the average particle size of the first group is greater than the average particle size of the third group so that the first porous network has an average pore size that is greater than the average pore size of the third porous network.

2. The method of claim 1, wherein the second porous network forms a tissue contacting side of the stent.

3. The method of claim 1, additionally comprising depositing a therapeutic substance in the first porous network, wherein the second porous network reduces the rate of release of the substance from the stent after the stent has been implanted in a body of a patient.

4. The method of claim 1, additionally comprising depositing a polymeric film layer on the second porous network.

5. The method of claim 1, wherein the particles of the second group are attached all the way around the first porous network such that the second porous network completely surrounds the first porous network.

6. A method of manufacturing a stent, comprising:
forming a first porous region;
forming a second porous region disposed over a portion of the first porous region;
forming a third porous region over a portion of the first porous region such that the first porous region is between the second and third porous regions; and
depositing a therapeutic substance in the first porous region, wherein an average pore size of the second porous region is less than an average pore size of the first porous region.

7. The method of claim 6, additionally including depositing a film layer over the second porous region.

8. The method of claim 7, wherein the film layer comprises a biodegradable polymer.

9. The method of claim 7, wherein the film layer comprises a non-degradable polymer.

10. The method of claim 7, wherein the film layer includes a second therapeutic substance.

11. The method of claim 7, wherein the film layer has a thickness from about 0.0001 inches to about 0.002 inches.

12. The method of claim 6, wherein the therapeutic substance is for the treatment of restenosis.

13. The method of claim 6, wherein the first or second porous region is formed by sintering particles.

14. The method of claim 6, wherein the first or second porous region is formed by sintering a matrix of overlapping filaments.

15. The method of claim 6, wherein the first or second porous region is formed by sintering woven wire fibers.

16. The method of claim 6, wherein the first porous region is formed by sintering particles having a first average diameter, and the second porous region is formed by sintering particles having a second average diameter, wherein the first average diameter is larger than the second average diameter.

17. The method of claim 16, wherein the first average diameter is 10 to 20 microns.

18. The method of claim 16, wherein the second average diameter is 2 to 4 microns.

19. A method of manufacturing a stent, comprising:
forming a first porous region;
forming a second porous region disposed over a first portion of the first porous region;
forming a third porous region disposed over a second portion of the first porous region; and
depositing a therapeutic substance in the first porous region, wherein an average pore size of the second porous region and an average pore size of the third porous region is less than an average pore size of the first porous region for reducing a rate of release of the therapeutic substance from the first porous region after the stent has been implanted in a vessel.

20. A method of manufacturing a strut element for a stent, comprising:
placing metallic particles having an average first diameter in contact with each other;
sintering the metallic particles having the average first diameter to form an inner core;
placing metallic particles having an average second diameter on the inner core; and
sintering the metallic particles having the average second diameter to form a porous outer layer.

21. The method of claim 20, wherein the average second diameter is less than the average first diameter.

22. The method of claim 20, further comprising depositing a therapeutic substance in the inner core.

23. A method of manufacturing a sintered sheet element for a stent, comprising:
placing metallic particles having an average first diameter to a first surface of a metallic core layer;
placing metallic particles having an average second diameter to a second surface of the metallic core layer;
sintering the metallic particles having the average first diameter to form a first porous outer layer; and
sintering the metallic particles having the average second diameter to form a second porous outer layer.

24. The method of claim 23, wherein the first and second porous outer layers are on opposing sides of the metallic core layer.

25. The method of claim 23, wherein the metallic core layer is a porous substrate.

26. The method of claim 25, wherein an average pore size of the of the metallic core layer is less than an average pore size of the first and second porous outer layers.

27. The method of claim 23, wherein the metallic core layer is a solid substrate.

28. The method of claim 23, further comprising, after the formation of the first and second porous outer layers, applying a therapeutic agent to the first porous outer layer or the second porous outer layer so that the therapeutic agent is contained in pores of the first porous outer layer or the second porous outer layer.

29. The method of claim 23, further comprising, after the formation of the first and second porous outer layers, applying a first therapeutic agent to the first porous outer layer and a second therapeutic agent to the second porous outer layer so that the first therapeutic agent is contained in pores of the first porous outer layer and the second therapeutic agent is contained in pores of the first porous outer layer, the first and second therapeutic agents being different.

30. The method of claim 23, further comprising loading a therapeutic agent in spaces between the sintered metallic particles of the first porous layer or the second porous layer.

* * * * *